(12) United States Patent
Abe

(10) Patent No.: US 7,485,091 B2
(45) Date of Patent: Feb. 3, 2009

(54) ELECTRONIC ENDOSCOPE SYSTEM

(75) Inventor: Kazunori Abe, Saitama (JP)

(73) Assignee: Fujinon Corporation, Saitama-shi (JP)

( * ) Notice: Subject to any disclaimer, the term of this patent is extended or adjusted under 35 U.S.C. 154(b) by 306 days.

(21) Appl. No.: 11/528,576

(22) Filed: Sep. 28, 2006

(65) Prior Publication Data

US 2007/0070194 A1    Mar. 29, 2007

(30) Foreign Application Priority Data

Sep. 29, 2005    (JP) ............................. 2005-283496

(51) Int. Cl.
*A61B 1/04*    (2006.01)
(52) U.S. Cl. ...................... 600/109; 600/101; 600/118; 348/72
(58) Field of Classification Search ................. 600/101, 600/103, 109, 118; 348/72, 74, 159
See application file for complete search history.

(56) References Cited

U.S. PATENT DOCUMENTS

| | | | |
|---|---|---|---|
| 3,986,498 A * | 10/1976 | Lewis ......................... | 600/508 |
| 4,398,297 A | 8/1983 | Hwang et al. | |
| 5,361,203 A * | 11/1994 | Hiyama et al. .............. | 385/117 |
| 6,589,162 B2 * | 7/2003 | Nakashima et al. .......... | 600/109 |
| 6,612,981 B2 * | 9/2003 | Onishi et al. ................ | 600/118 |
| 6,902,529 B2 * | 6/2005 | Onishi et al. ................ | 600/118 |
| 7,048,686 B2 * | 5/2006 | Kameya et al. .............. | 600/179 |
| 2001/0015754 A1 | 8/2001 | Nakashima et al. | |
| 2002/0184122 A1 | 12/2002 | Yamaguchi et al. | |
| 2003/0197781 A1 | 10/2003 | Sugimoto et al. | |
| 2004/0082834 A1 * | 4/2004 | Onishi et al. ................ | 600/118 |
| 2004/0230094 A1 * | 11/2004 | Nakamura ................... | 600/101 |
| 2006/0217591 A1 * | 9/2006 | Abe ............................ | 600/118 |

FOREIGN PATENT DOCUMENTS

| | | |
|---|---|---|
| JP | 60-048011 A | 3/1985 |
| JP | 2001-046334 A | 2/2001 |

* cited by examiner

*Primary Examiner*—John P Leubecker
(74) *Attorney, Agent, or Firm*—Birch, Stewart, Kolasch & Birch, LLP

(57) ABSTRACT

In an electronic endoscope system, an individual channel of a frequency band is allocated to each of a plurality of electronic endoscopes. When a release switch of the electronic endoscope is operated to record an endoscopic image, a picture signal of the endoscopic image is modulated into a radio frequency signal, and a header representative of the allocated channel is attached to the radio frequency signal, before sending it as an electric wave to a storage server through the allocated channel. The storage server is provided with a plurality of data storages for the individual channels. In the storage server, the received radio frequency signal is demodulated into the original picture signal, and an I/O port sorts the picture signal according to the attached header, to write it as the endoscopic image in the data storage corresponding to the channel represented by the attached header.

5 Claims, 6 Drawing Sheets

ELECTRONIC ENDOSCOPE SYSTEM

FIELD OF THE INVENTION

The present invention relates to an electronic endoscope system consisting of a plurality of electronic endoscopes and processors, which communicate signals using electric waves.

BACKGROUND OF THE INVENTION

Medical diagnoses utilizing an electronic endoscope have widely been practiced in the medical field these days. The electronic endoscope has an imaging device like a CCD, which is built in an end of an elongated probing portion that is introduced into a body cavity, so that the CCD takes an image signal from an internal body site. The image signal is processed in a processor, to display an image of the internal body site, called an endoscopic image, on a monitor.

The electronic endoscope and the processor are usually connected to each other through a signal cable. Also, wireless electronic endoscopes systems have been suggested, for example, in Japanese Laid-open Patent Application Nos. Sho 60-48011 and 2001-046334. In the wireless electronic endoscope system, the electronic endoscope is provided with a modulator and a sender for sending the modulated signal as an electric wave, whereas the processor is provided with a receiver for receiving the electric wave and a demodulator for demodulating the modulated signal. Because the signal is communicated by way of the electric wave, the signal cable is unnecessary, so the handling of the wireless electronic endoscope is superior to those using the signal cable.

In addition to the above-mentioned advantage that the signal cable does not give limit to the handling of the electronic endoscope, and thus the workability is improved, the wireless electronic endoscope system has another advantage. Since there is not any electric connection between the electronic endoscope and the processor, it is unnecessary to maintain a high dielectric strength voltage of about 4 kV between a patient circuit and a secondary circuit, while such a high dielectric strength voltage is necessary for the conventional electronic endoscope system using the signal cable.

In practice, it is usual to install a number of electronic endoscope systems together in a specific treatment room in a hospital, so that these systems allow endoscopic diagnoses individually. It has, therefore, been suggested to provide a supervisory system for managing data and results of diagnoses obtained at the respective systems, including endoscopic images. However, as for the wireless electronic endoscope systems that communicate signals by way of electric waves, such a supervisory system has not yet been suggested.

SUMMARY OF THE INVENTION

In view of the foregoing, a primary object of the present invention is to provide a wireless electronic endoscope system that communicates signals by way of electric waves, and supervises results of diagnoses obtained based on a lot of endoscopic images taken by a plurality of electronic endoscopes.

To achieve the above and other objects in an electronic endoscope system comprising a plurality of electronic endoscopes, each of the electronic endoscopes comprises an imaging device for obtaining an image signal from a site to observe inside a body cavity; a device for digitalizing the image signal into a picture signal and producing a radio frequency signal from the picture signal through quadrature modulation; a control member manually operated to enter a command for recording the picture signal as an endoscopic image; a sender for sending the radio frequency signal as an electric wave, wherein an individual channel of a frequency band for the electric wave is allocated to each of the electronic endoscopes; and a header attaching section for attaching a header to the radio frequency signal when the control member is operated, the header being representative of the channel allocated to the electronic endoscope for sending the radio frequency signal.

The electronic endoscope system of the present invention further comprises a data supervising apparatus for supervising diagnostic data including the endoscopic images obtained through the electronic endoscopes. The data supervising apparatus comprises a receiver for receiving the radio frequency signals as the electric waves from the electronic endoscopes; a demodulator for demodulating the radio frequency signals into the original picture signals; a signal processing device for producing the endoscopic images from the picture signals; an input-output controller for sorting the endoscopic images according to the channels represented by the headers attached to the radio frequency signals; and a plurality of data storages provided for the individual channels, to record and store the endoscopic images as sorted by the input-output controller.

Preferably, the electronic endoscopes and the receiver communicate the electronic waves in a polling method.

It is also preferable to provide each of the electronic endoscopes with a scrambler for scrambling the picture signal. In that case, the data supervising apparatus should be provided with a descrambler for descrambling the picture signal.

Since a channel of a frequency band is allocated to each of the electronic endoscopes, and the header representative of the allocated channel is attached to the radio frequency signal when it is sent out from the individual electronic endoscope, it is possible to sort out the endoscopic image according to the allocated channel, and store it in one of the data storages that is prepared for the allocated channel. Thus, the endoscopic images obtained through the individual electronic endoscopes may be managed by the single data supervising apparatus.

Providing the scrambler in each of the electronic endoscopes and the descrambler in the data supervising apparatus improves security against peeking of the obtained endoscopic images and thus prevents invasion of patients' privacy.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
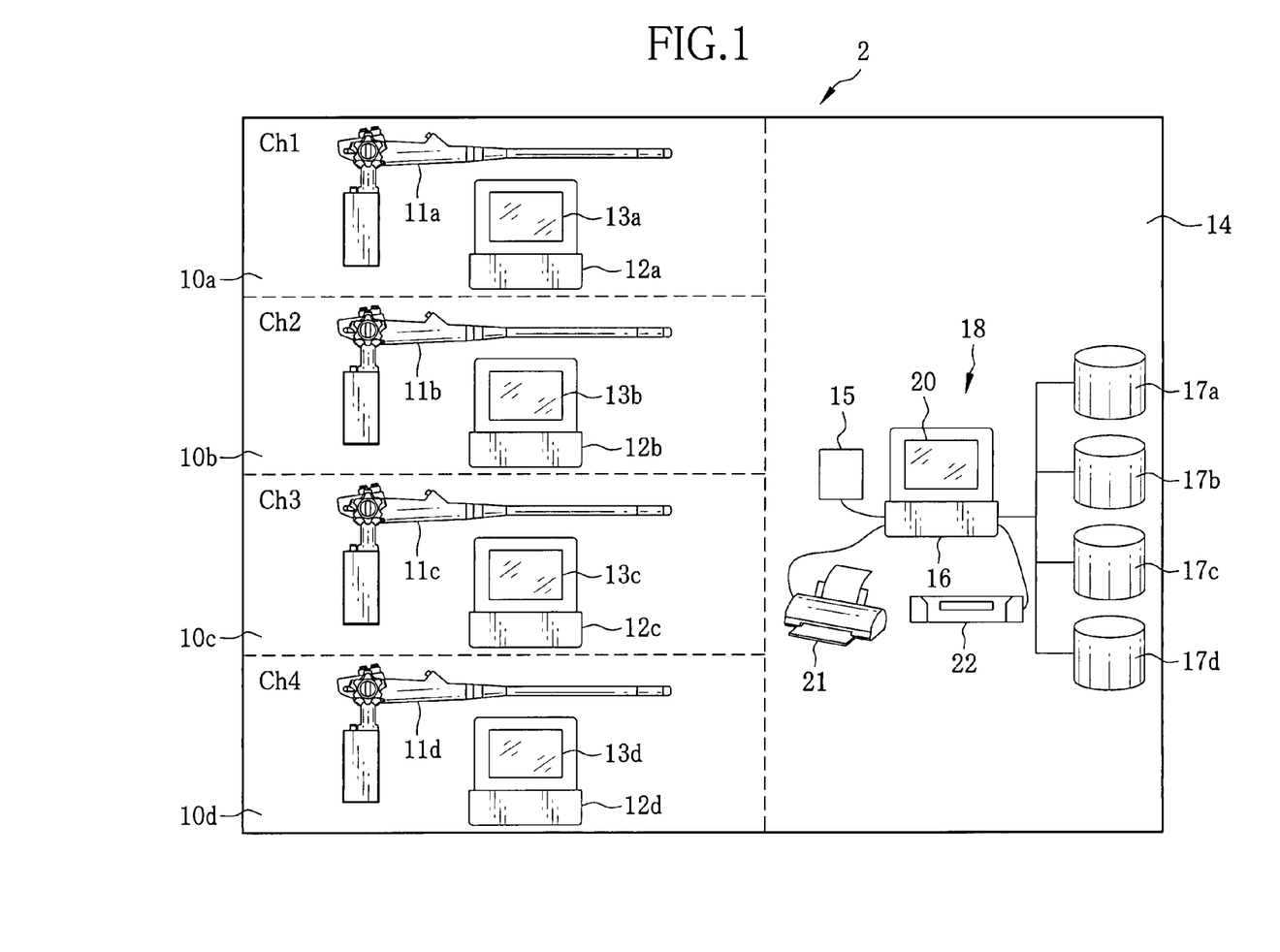
FIG. 1 is a schematic diagram illustrating an electronic endoscope system according to an embodiment of the present invention.

FIG. 1 shows an electronic endoscope system 2, which consists of four electronic endoscopes 11a, 11b, 11c and 11d, four processors 12a, 12b, 12c and 12d, and four monitors 13a, 13b, 13c and 13d, which are installed in examination rooms 10a, 10b, 10c and 10d respectively, and a storage server 18 installed in a supervising room 14 that is distant from the examination rooms 10a to 10d. The storage server 18 consists of a receiver unit 15, a supervisory personal computer 16, and data storages 17a, 17b, 17c and 17d. In the examination room 10a, 10b, 10c or 10d, a doctor examines a patient, using the electronic endoscope 11a, 11b, 11c or 11d.

In the electronic endoscope system 2, signals are communicated between the electronic endoscopes 11a to 11d, on one hand, and the associated processors 12a to 12d, on the other hand, using four channels Ch1, Ch2, Ch3 and Ch4 of frequency bands of electric waves 19 (see FIGS 3 and 5), respectively. Also, signals are communicated by way of electric waves 19 between the electronic endoscopes 11a to 11d and the receiver unit 15, as well as between the processors 12a to 12d and the receiver unit 15. The data storages 17a to 17d store data of endoscopic images obtained through the electronic endoscopes 11a to 11d, respectively. A monitor 20, a printer 21 and a video recorder 22 are connected to the personal computer 16. According to commands entered by the operator, the stored endoscopic images may be displayed on the monitor 20, a hard copy of the endoscopic image may be printed out through the printer 21, or videos of the endoscopic images are recorded on the video tape recorder 22. Thus, the results of endoscopic diagnoses are comprehensively managed. Note that the individual electronic endoscopes 11a to 11d have the same structure, so do the individual processors 12a to 12d. Accordingly, the following description will refer to the electronic endoscope 11a and the processor 12a as representative examples.

Figure 2:
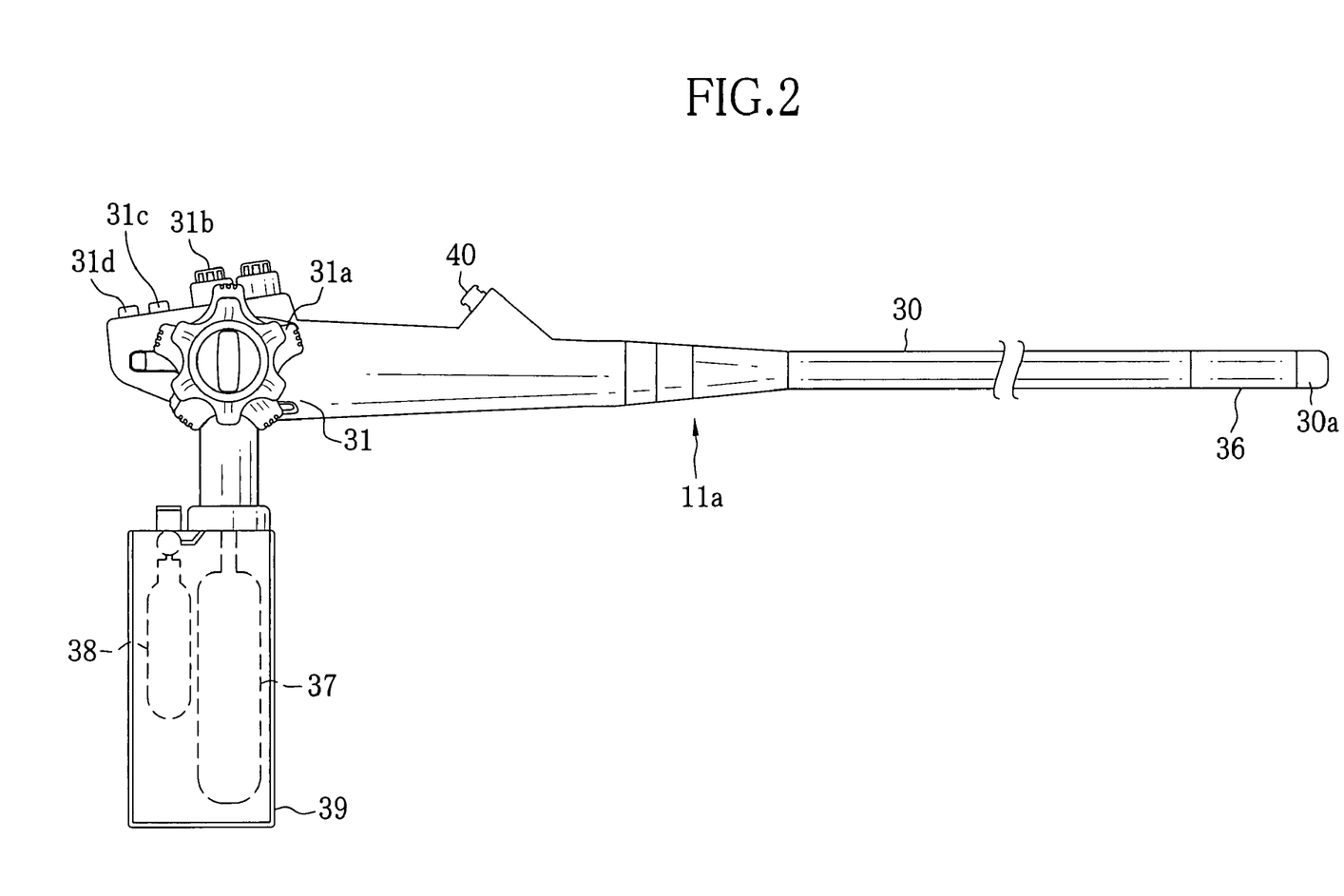
FIG. 2 is a schematic diagram illustrating an electronic endoscope of the system.
Figure 3:
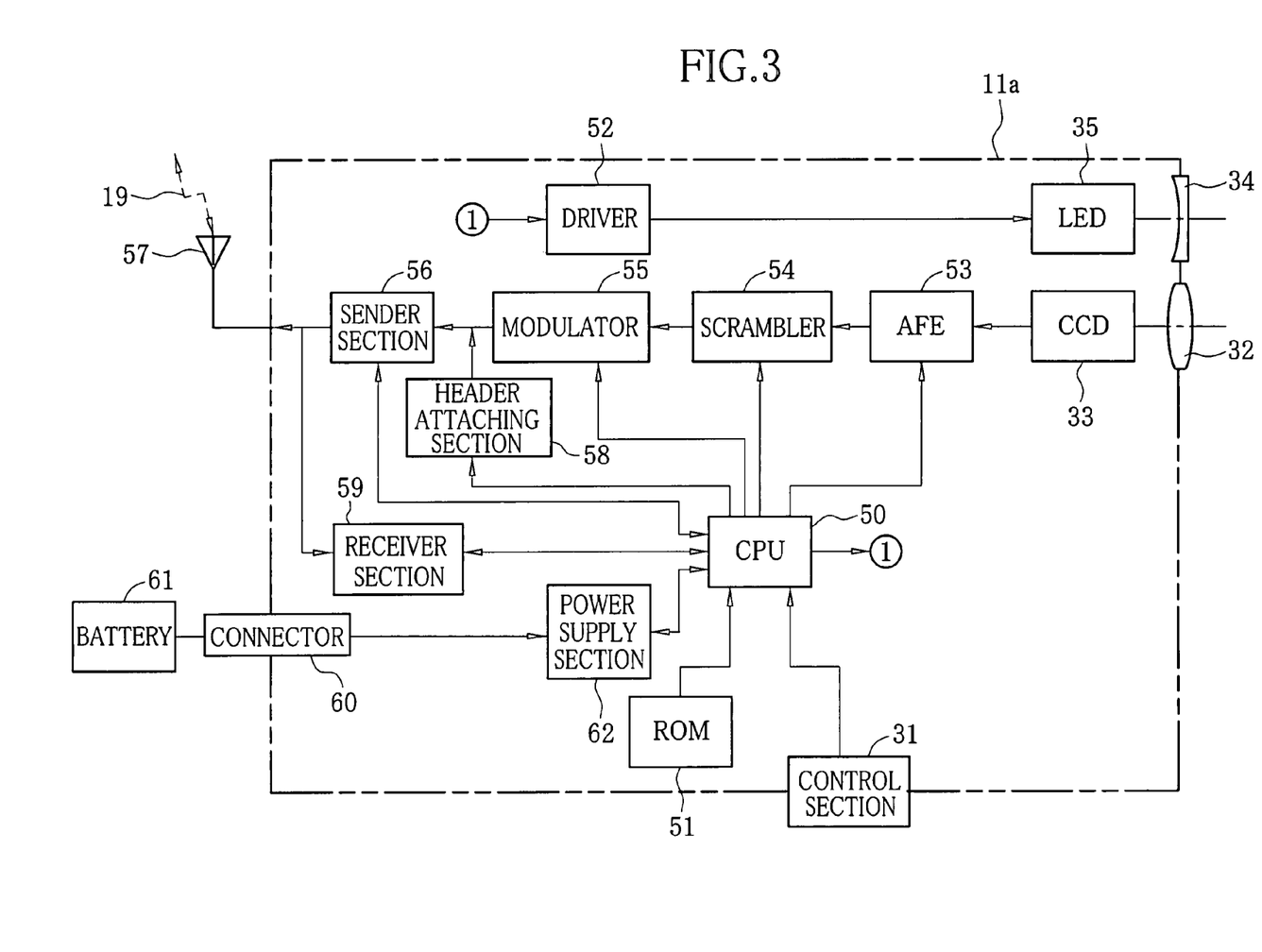
FIG. 3 is a block diagram illustrating an internal structure of the electronic endoscope.

In FIG. 2, the electronic endoscope 11a is provided with a probing portion 30 that is introduced into a body cavity, and a control section 31 that is joined to a base end of the probing portion 30. Built in a probe tip 30a, which is joined to a distal end of the probing portion 30, are an objective lens 32 for forming an optical image of an internal body part to be observed, a CCD 33 as an imaging device for capturing the optical image of the internal body part, an illuminative lens 34, and an LED light source 35 for illuminating the body cavity, as shown in FIG. 3.

Behind the probe tip 30a is provided a curving section 36 consisting of a number of linked curving segments. By operating an angle knob 31a on the control section 31, a number of wires, which are not shown but extend in the probing portion 30, are pulled and pushed to curve the curving section 36 appropriately, thereby to direct the probe tip 30a to an aimed point inside the body cavity.

A cartridge 39, in which a water tank 37 containing water and an air cylinder 38 containing air are built, is detachably attached to a position below the control section 31. In cooperation with an action on a watering/airing switch 31b of the control section 31, the water contained in the water tank 37 and the air contained in the air cylinder 38 are fed through a water pipe and an air pipe and ejected from a wash nozzle toward the objective lens 32, though the water pipe and the air pipe are not shown but disposed in the electronic endoscope 11a, and the wash nozzle is not shown but formed through the probe tip 30a. Thereby, dirt on the surface of the objective lens 32 is washed away, and the air is sent to the body cavity. The cartridge 39 is so positioned that the wrist of the operator is held on the cartridge 39 to stabilize the electronic endoscope 11a on operating it. Designated by 40 is an inlet for inserting a treatment tool.

Beside the angle knob 31a and the watering/airing switch 31b, the control section 31 is provided with a freeze switch 31c, a release switch 31d. The freeze switch 31c is operated to capture a still image from the endoscopic image. The release switch 31d is operated to record the still image.

Referring to FIG. 3, the overall operation of the electronic endoscope 11a is under the control of a CPU 50. A ROM 51 storing various programs and data for controlling the operation of the electronic endoscope 11a is connected to the CPU 50. The CPU 50 reads out necessary program and data from the ROM 51, to control the operation of the electronic endoscope 11a based on the read program and data.

A driver 52 is connected to the LED 35. The driver 52 turns the LED 35 on and off under the control of the CPU 50. The light emitted from the LED 35 is projected through the illuminative lens 34 onto the internal body part to observe. Note that the LED 35 is not necessarily located in the probe tip 30a, but may be located in an intermediate portion inside the control section 31. In that case, the light from the LED 35 is guided through a light guide to the probe tip 30a.

An optical image of the internal body part is formed through the objective lens 32 on an imaging surface of the CCD 33, so the CCD 33 outputs from individual pixels analog image signals corresponding to the optical image. The analog image signals are fed to an AFE (analog front end) circuit 53, where the analog image signals are subjected to correlated double sampling, and are amplified and converted into a digital picture signal.

A scrambler 54 scrambles the digital picture signal as an output of the AFE circuit 53, thereby to output a coded or ciphered picture signal. A modulator 55 produces a radio frequency (RF) signal from the digital picture signal as the output of the AFE circuit 53, for example, through digital quadrature modulation. A sender section 56 sends the radio frequency signal as the electric wave 19 through an antenna 57 to the processor 12a and the receiver unit 15.

A head attaching section 58 attaches a header to the radio frequency signal as produced from the modulator 55, wherein the header allocates the first channel Ch1 to the radio frequency signal in the first endoscope 11a. The RF signal attached by the header is temporarily stored in a not-shown buffer that is built in the sender section 56.

Figure 5:
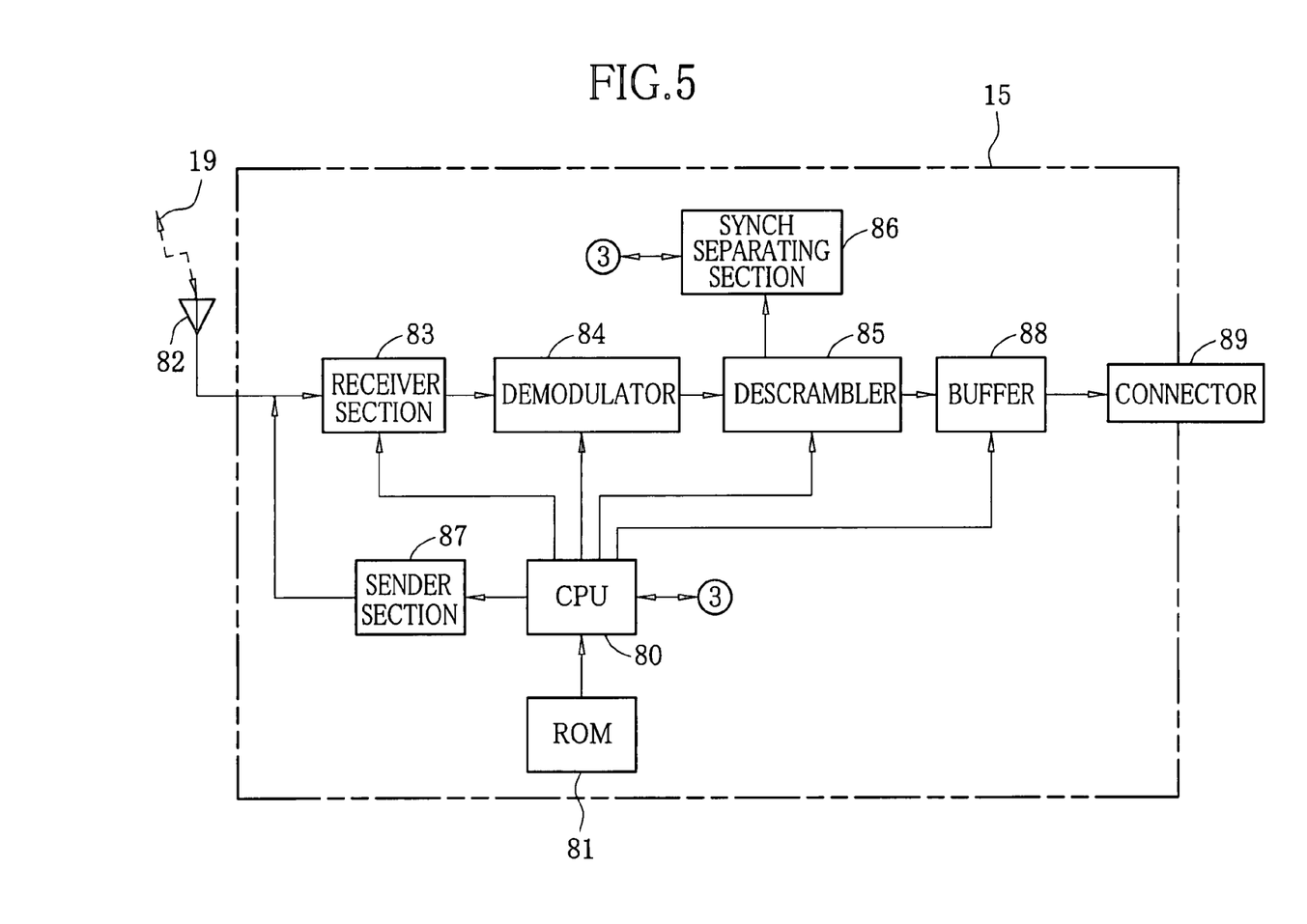
FIG. 5 is a block diagram illustrating an internal structure of a receiver of the system.

A receiver section 59 receives through the antenna 57 a polling signal that is sent from a sender section 87 of the receiver unit 15 (see FIG. 5). The RF signal, having been attached by the header and stored temporarily in the buffer of the sender section 56, is sent as the electric wave 19 from the sender section 56 to the receiver unit 15, upon receipt of the polling signal on the receiver section 59.

A connector 60 is connected to batteries 61. The electric power from the batteries 61 is supplied through a power supply section 62 to the respective components of the electronic endoscope 11a under the control of the CPU 50. Although it is omitted from the drawings, a battery chamber for loading the batteries 61 is formed behind the control section 31, and the connector 60 is located inside the battery chamber.

Figure 4:
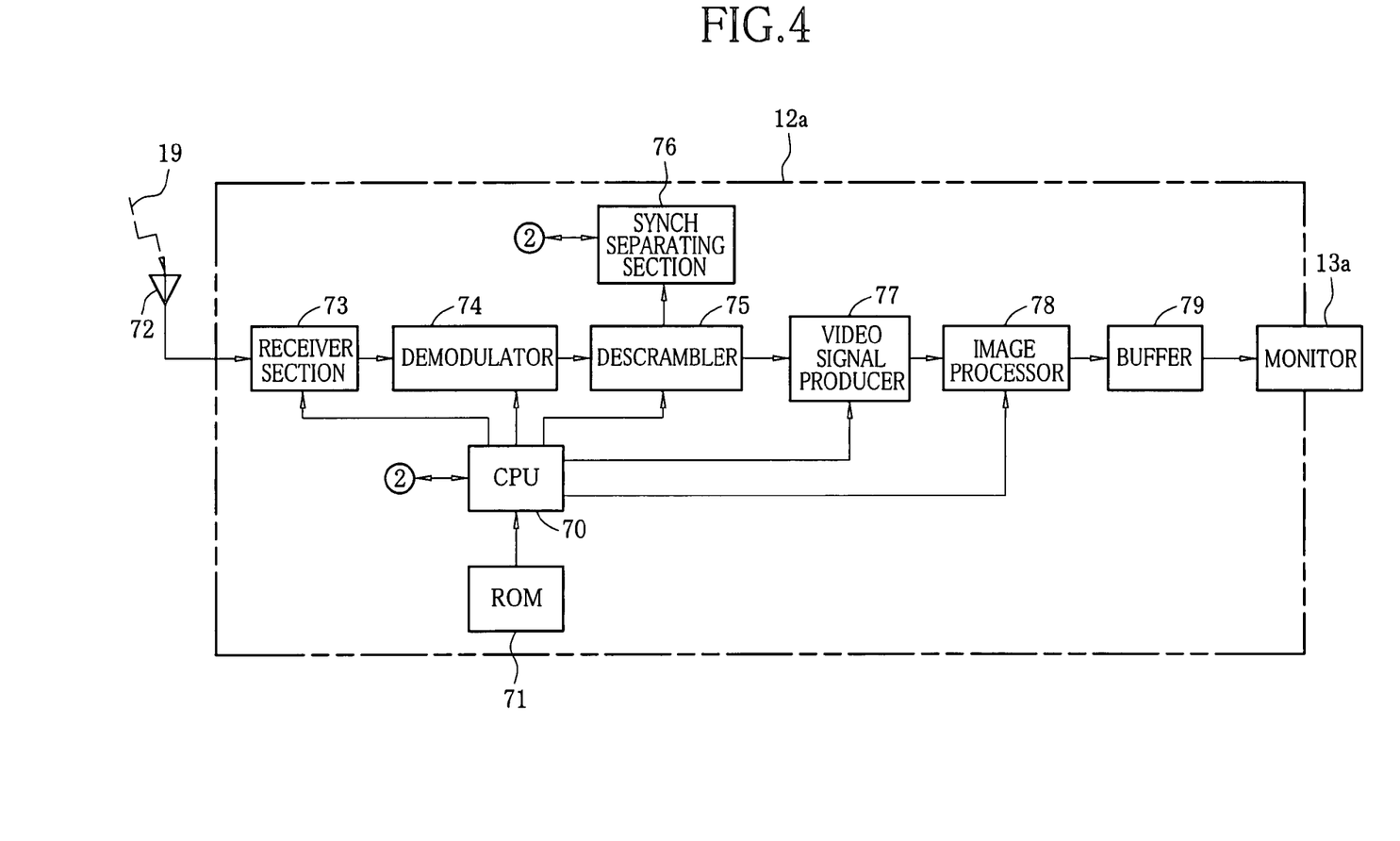
FIG. 4 is a block diagram illustrating an internal structure of a processor of the system.

FIG. 4 shows the structure of the processor 12a, wherein a CPU 70 controls overall operations of the processor 12a. The CPU 70 is connected to a ROM 71 that stores various programs and data for controlling the operations of the processor 12a. The CPU 70 reads out necessary ones of these programs and data from the ROM 71, writes them on a not-shown built-in RAM, and controls the operation of the processor 12a based on the read program and data.

An antenna 72 receives the electric wave 19. The electric wave 19 from the electronic endoscope 11a as received on the antenna 72, i.e. the radio frequency signal, is amplified at a receiver section 73. A demodulator 74 demodulates the original picture signal before being modulated in the electronic endoscope 11a, for example, by subjecting the radio frequency signal to digital quadrature detection.

A descrambler 75 descrambles the digital picture signal as an output of the demodulator 74, thereby to decipher the picture signal. Under the control of the CPU 70, a synch separating section 76 carries out amplitude separation to separate a synchronizing signal from the picture signal as an output of the descrambler 75. Thereafter, the synch separating section 76 carries out frequency separation for separating the horizontal synchronizing signal and the vertical synchronizing signal.

A video signal producer 77 produces a digital video signal from the picture signal. An image processor 78 treats the video signal, as produced from the video signal producer 77, with various kinds of image-processing, such as masking and character data attaching. A buffer 79 temporarily stores the video signal as processed in the image processor 78, and the video signal is used for displaying an endoscopic image on the monitor 13a.

FIG. 5 shows the structure of the receiver unit 15, wherein a CPU 80 controls overall operations of the receiver unit 15. The CPU 80 is connected to a ROM 81 that stores various programs and data for controlling the operations of the receiver unit 15. The CPU 80 reads out necessary ones of these programs and data from the ROM 81, writes them on a not-shown built-in RAM, and controls the operation of the receiver unit 15 based on the read program and data.

An antenna 82 receives the electric wave 19. The electric wave 19 from the electronic endoscopes 11a to 11d as received on the antenna 82, i.e. the radio frequency signal attached by the header that indicates the allocated channel, is amplified at a receiver section 83. A demodulator 84 demodulates the radio frequency signal into the original picture signal before being modulated in the electronic endoscope 11a, for example, by subjecting the radio frequency signal to digital quadrature detection.

A descrambler 85 descrambles the digital picture signal as an output of the demodulator 84, to decipher the picture signal. Under the control of the CPU 80, a synch separating section 86 carries out amplitude separation to separate a synchronizing signal from the picture signal as an output of the descrambler 85. Thereafter, the synch separating section 86 separates the horizontal synchronizing signal and the vertical synchronizing signal through frequency separation.

A sender section 87 sends out the polling signals from the antenna 82 seriatim to the individual electronic endoscopes 11a to 11d cyclically at constant intervals. A buffer 88 temporarily stores the picture signal as an output of the descrambler 85. The picture signal temporarily stored in the buffer 88 is sent to the personal computer 16 through a cord that is connected to a connector 89.

Figure 6:
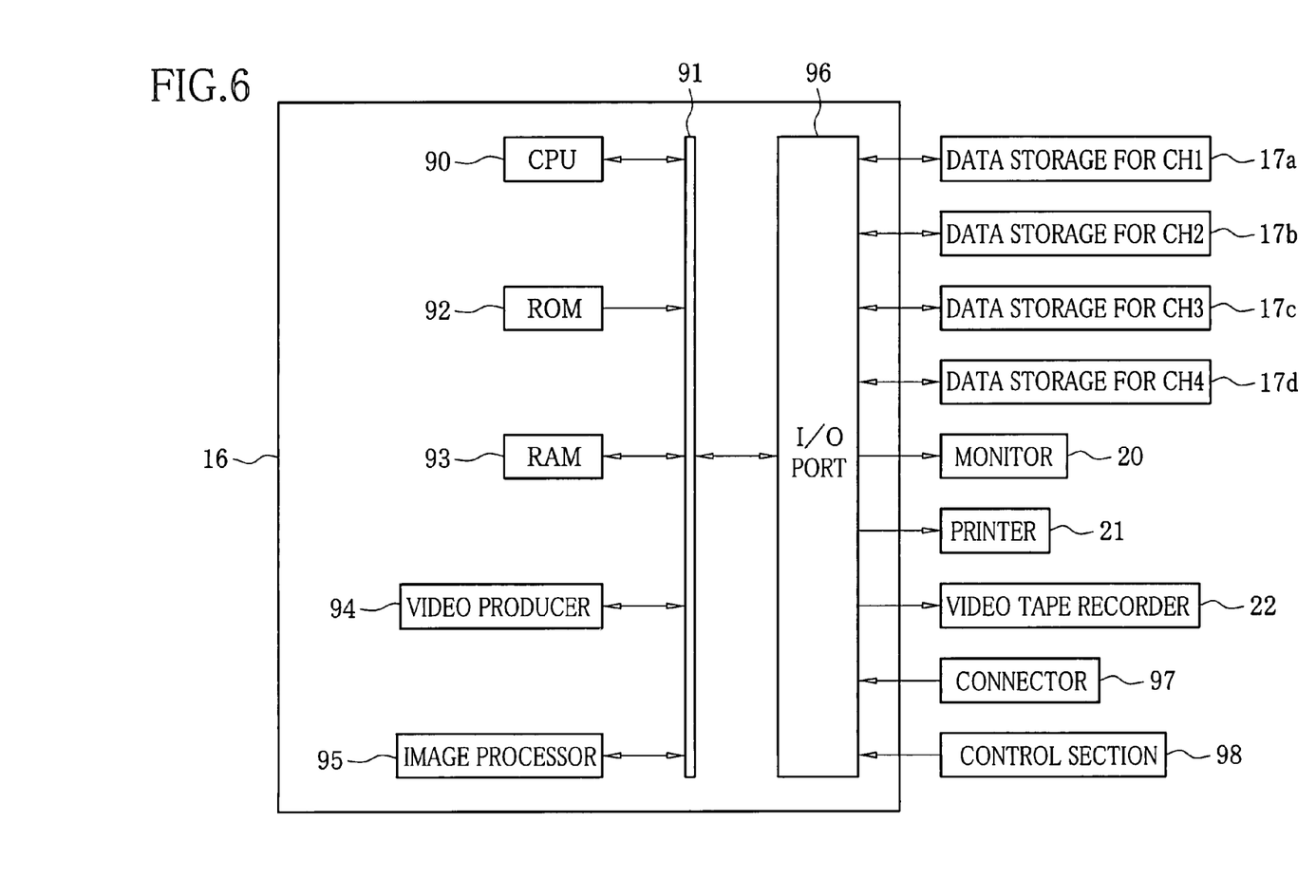
FIG. 6 is a block diagram illustrating an internal structure of a supervising computer of the system.

As shown in FIG. 6, the overall operation of the personal computer 16 is under the control of a CPU 90. The CPU 90 is connected through a bus 91 to a ROM 92 that stores various programs and data for controlling the operation of the personal computer 16. The CPU 90 reads out necessary programs and data from the ROM 92 and writes them on a RAM 93, to control the operation of the personal computer 16.

A video signal producer 94 produces a digital video signal from the picture signal, like the vide signal producer 77 of the processor 12a. An image processor 95 treats the video signal, as produced from the video signal producer 94, with various kinds of image-processing, such as masking and character data attaching.

The bus 91 is connected to an I/O port 96, which is connected to the data storages 17a to 17d for the four channels Ch1 to Ch4, the monitor 20, the printer 21 and the video tape recorder 22. Also, a connector 97 and a control section 98 including a keyboard and a mouse are connected to the I/O port 96. The connector 97 is connected to the connector 89 of the receiver unit 15

In order to determine the signal channel allocated to the electronic endoscope 11a, 11b, 11c or 11d that is used to obtain the received endoscopic image, the I/O port 96 analyzes contents of the header as attached to the endoscopic image, and sends the data of the endoscopic image to the data storage 17a, 17b, 17c or 17d for the determined signal channel. Also, in response to a command entered through the control section 98, such as a display command, a print command, or a command for video-recording of the endoscopic image, the I/O port 96 reads out the data of the endoscopic image from the data storage 17a, 17b, 17c or 17d of the designated signal channel, and sends the data to the appropriate component.

To observe a body cavity with the electronic endoscope system 2, first the LED light source 35 is turned on, and the probing portion 30 is introduced into the body cavity, to take endoscopic images through the CCD 33 while illuminating the inside of the body cavity. The taken endoscopic images are observable on the monitor 13a.

Concretely, an optical image of a body part inside the body cavity is formed on the imaging surface of the CCD 33 through the objective lens 32, so the CCD 33 outputs image signals corresponding to the optical image. The analog image signals are subjected to correlated-double-sampling, and are amplified and converted into a digital picture signal at the AFE 53.

The digital picture signal, as output from the AFE 53, is ciphered through the scrambling in the scrambler 54, and is subjected to digital quadrature modulation in the modulator 55, thereby to produce the radio frequency signal. The radio frequency signal is amplified at the sender section 56, and then sent as the electric wave 19 from the antenna 57.

On the other hand, the electric wave 19 from the antenna 57 is received at the antenna 72 of the processor 12a, and is amplified as the radio frequency signal in the receiver section 73. The demodulator 74 subjects the amplified radio frequency signal to digital quadrature detection, to demodulate the radio frequency signal into the original picture signal before being modulated in the electronic endoscope 11a.

The picture signal demodulated in the demodulator 74 is subjected to the descrambling in the descrambler 75 and, thereafter, to the synch separation processes in the synch separating section 76 under the control of the CPU 70. The video signal producer 77 produces the digital video signal from the picture signal. The video signal is subjected to various kinds of image-processing in the image processor 78. The processed video signal is stored temporarily in the buffer 79, and is displayed as the endoscopic images on the monitor 13a.

Next, a processing sequence executed in response to the operation on the release switch 31d of the control section 31 will be described.

When the release switch 31d is operated, a control signal is output from the release switch 31d and is sent to the CPU 50. Responsive to the control signal from the release switch 31d, the CPU 50 activates the header attaching section 58 to attach the header representative of the first channel Ch1 to the RF signal as being output from the modulator 55 at that time. The RF signal attached by the header is temporarily stored in the buffer of the sender section 56.

In the receiver unit 15, on the other hand, the sender section 87 sends out the polling signals from the antenna 82 seriatim to the individual electronic endoscopes 11a to 11d cyclically at constant intervals. When the electronic endoscope 11a receives the polling signal at the receiver section 59, the electronic endoscope 11a sends out the RF signal, which is stored in the buffer of the sender section 56, as the electric wave 19 to the receiver unit 15.

Upon receipt of the electric wave 19 from the electronic endoscope 11a at the receiver section 83, the receiver unit 15 subjects the RF signal to digital quadrature detection in the demodulator 84, to demodulate it into the original picture signal.

The picture signal from the demodulator 84 is subjected to the descrambling process in the descrambler 85, and then to the synch separation in the synch separating section 86, and is stored temporarily in the buffer 88. The picture signal stored in the buffer 88 is sent to the personal computer 16 through the cord that is interconnected between the connectors 89 and 97.

As described above, the electronic endoscopes 11a to 11d are respectively provided with the scramblers 54, whereas the processors 12a to 12d and the receiver unit 15 are respectively provided with the descramblers 75 and 85. Therefore, peeking of the obtained endoscopic images is securely prevented, so the electronic endoscopic system 2 of the present invention provides secure protection against the invasion of patients' privacy.

In the personal computer 16, the picture signal received from the receiver 16 through the connector 89, is converted into the digital video signal through the video signal producer 94. The video signal produced from the video signal producer 94 is subjected to various kinds of image-processing in the image processor 95, thereby to produce the endoscopic image.

The produced endoscopic image is analyzed by the I/O port 96 to determine the contents of the attached header, and is sent to and written in the one of the data storages 17a to 17d that is prepared for the channel designated by the attached header. Thus, the endoscopic images obtained through the individual electronic endoscopes 11a to 11d are sorted out and stored respectively in the data storages 17a to 17d of the corresponding channels.

When the control section 98 is operated to enter the command for displaying the endoscopic image, the printing command, or the video recording command, the data of the designated endoscopic image is read out from the corresponding data storage, and is sent to the corresponding component through the I/O port 96.

Although the present invention has been described with respect to the preferred embodiment, the present invention is not to be limited to the above embodiment. On the contrary, various modifications will be possible without departing from the scope of claims appended hereto.

What is claimed is:

1. An electronic endoscope system comprising a plurality of electronic endoscopes, each of said electronic endoscopes comprising:

an imaging device for obtaining an image signal from a site to observe inside a body cavity;

a device for digitalizing the image signal into a picture signal and producing a radio frequency signal from the picture signal through quadrature modulation;

a control member manually operated to enter a command for recording the picture signal as an endoscopic image;

a sender for sending the radio frequency signal as an electric wave, wherein an individual channel of a frequency band for the electric wave is allocated to each of said electronic endoscopes; and a header attaching section for attaching a header to the radio frequency signal when said control member is operated, said header being representative of the channel allocated to said electronic endoscope for sending the radio frequency signal; and wherein said electronic endoscope system comprises a data supervising apparatus for supervising diagnostic data including the endoscopic images obtained through said electronic endoscopes, said data supervising apparatus comprising:

a receiver for receiving the radio frequency signals as the electric waves from said electronic endoscopes;

a demodulator for demodulating the radio frequency signals into the original picture signals;

a signal processing device for producing the endoscopic images from the picture signals;

an input-output controller for sorting the endoscopic images according to the channels represented by the headers attached to the radio frequency signals; and a plurality of data storages provided for the individual channels, to record and store the endoscopic images as sorted by said input-output controller.

2. An electronic endoscope system as claimed in claim 1, wherein said electronic endoscopes and said data supervising apparatus communicate the electronic waves in a polling method.

3. An electronic endoscope system as claimed in claim 1, wherein each of said electronic endoscopes further comprises a scrambler for scrambling the picture signal, whereas said data supervising apparatus further comprises a descrambler for descrambling the picture signal.

4. An electronic endoscope system as claimed in claim 3, wherein said receiver, said demodulator, said descrambler and a sender for sending polling signals seriatim to said electronic endoscopes are integrated into a unit having a CPU for controlling respective components of said unit, whereas said signal processing device and said input-output controller are installed in a personal computer, to which said unit and said data storages are connected.

5. An electronic endoscope system as claimed in claim 1, further comprising a processor for each channel, said processor receiving the radio frequency signal as the electric wave from a corresponding one of said electronic endoscopes, and processing the radio frequency signal so as to display the endoscopic image as obtained through the corresponding electronic endoscope on a monitor.

* * * * *